United States Patent
Lucas, Jr. et al.

(10) Patent No.: US 7,159,608 B1
(45) Date of Patent: Jan. 9, 2007

(54) MANIFOLD SYSTEM AND METHOD FOR COMPRESSED MEDICAL GASES

(75) Inventors: James L. Lucas, Jr., Elyria, OH (US); Donald M. Simo, Vermilion, OH (US)

(73) Assignee: Tri-Tech Medical Inc., Avon, OH (US)

( * ) Notice: Subject to any disclaimer, the term of this patent is extended or adjusted under 35 U.S.C. 154(b) by 515 days.

(21) Appl. No.: 10/703,692

(22) Filed: Nov. 7, 2003

Related U.S. Application Data (60) Provisional application No. 60/424,552, filed on Nov. 7, 2002.

(51) Int. Cl.
*F16K 49/00* (2006.01)
(52) U.S. Cl. .................. 137/341; 137/557; 251/143; 165/47
(58) Field of Classification Search ............... 137/341, 137/557; 251/143; 165/47
See application file for complete search history.

(56) References Cited

U.S. PATENT DOCUMENTS

| | | | | |
|---|---|---|---|---|
| 1,988,289 A | * | 1/1935 | Wittemann | 261/128 |
| 3,770,938 A | * | 11/1973 | Agarate | 392/488 |
| 3,871,371 A | * | 3/1975 | Weigl | 128/204.17 |
| 3,990,441 A | * | 11/1976 | Hoyt et al. | 128/200.18 |
| 4,305,388 A | * | 12/1981 | Brisson | 128/204.17 |
| 4,621,633 A | * | 11/1986 | Bowles et al. | 128/203.17 |
| 6,305,400 B1 | * | 10/2001 | Simo et al. | 137/14 |

* cited by examiner

*Primary Examiner*—A. Michael Chambers
(74) *Attorney, Agent, or Firm*—Christopher L. Parmelee; Walker & Jocke LPA (57) ABSTRACT

A manifold system is provided herein. The manifold is operative to automatically switch between an In-Use supply of compressed gas to a Reserve supply of compressed gas. The manifold system is constructed so that after it has been installed, it may be converted for use in other applications such as between compressed gas cylinders and portable bulk liquefied gas. The system may include low wattage electric heater which are mechanically held in direct contact with the valve seat body housing of the primary regulators. The direct contact of the heaters with the valve seat is operative to prevent the primary regulator valve seat from freezing up. The manifold system may include transducers at a plurality of points in the system. A processor is operative to control one or more solenoids to switch supplies of compressed gas and to trigger alarms responsive to the outputs of the transducers.

14 Claims, 8 Drawing Sheets

MANIFOLD SYSTEM AND METHOD FOR COMPRESSED MEDICAL GASES

This application claims the benefit of U.S. Provisional Application No. 60/424,552 filed on Nov. 7, 2002.

TECHNICAL FIELD

This invention relates to the supply of compressed gases. Specifically, this invention relates to a manifold system and method for compressed medical gases.

BACKGROUND ART

It is often necessary for trained personnel to provide a variety of gases in a medical facility or other type of facility. Examples of such gases include medical air, oxygen, nitrogen, nitrous oxide, and carbon dioxide. Systems are also often installed in medical facilities which provide vacuum or gas evacuation. Gas service may be provided through a system which delivers the gas throughout a facility or portions or zones thereof. A number of primary supply sources of gas are used to deliver gas through outlet ports positioned at locations within the medical facility. The delivery system for each type of gas commonly includes manifolds with appropriate shut-off valves and pressure gauges. The primary supply source for each gas may be located in a secure area in the interior of the medical facility. Alternatively a primary supply source may be located at the exterior of the facility for maintenance by outside vendors providing the various gases.

It is critically important that the correct gas at the proper pressure be continuously supplied by the medical gas supply system. Consequently there exists a need for a system of supplying compressed gases that is operative to minimize interruption of the supply of the compressed gases. There also exists a need for a system of supplying compressed gases which can efficiently activate alarms responsive to changes to the supply of compressed gases to the system. In addition, there exists a need for a system of supplying compressed gases which is convertible for use with a plurality of different sources of compressed gases. Further there exists a need for a system of supply compressed gases which is less costly to produce.

DISCLOSURE OF INVENTION

It is an object of an exemplary form of the present invention to provide a method and system of supplying compressed gases that is operative to minimize interruption of the supply of the compressed gases.

It is a further object of an exemplary form of the present invention to provide a method and system of supplying compressed gases which can efficiently activate alarms responsive to changes to the supply of compressed gases to the system.

It is a further object of an exemplary form of the present invention to provide a method and system of supplying compressed gases which is convertible for use with a plurality of different sources of compressed gases.

It is a further object of an exemplary form of the present invention to provide a method and system of supplying compressed gases which is less expensive to produce.

Further objects of the present invention will be made apparent in the following Best Mode for Carrying Out the Invention and the appended claims.

The foregoing objects are accomplished in an exemplary embodiment by a manifold that is operative to automatically switch between an "In-Use" supply of compressed gas to a "Reserve" supply of compressed gas. The manifold system may include a plurality of transducers at a plurality of points in the system. The system may include a logic board with a processor that is operative to control one or more solenoid valves to switch between the In-Use and Reserve supplies of compressed gas and to trigger alarms responsive to the output pressures of the compressed gases in the system being above or below predetermined alarm limits In the exemplary embodiment, the manifold system may be designed and built so that, after it has been installed, it may be converted for use in other applications or other supply sources including compressed gas cylinders, portable bulk liquefied gas, and different types of gases. For higher pressure compressed gas supplies, the system may include low wattage electric heaters which are mechanically held in direct contact with the valve seat body housing of the primary regulators. The direct contact of the heaters with the valve seat is operative to prevent the primary regulator valve seat from freezing up.

In one exemplary configuration of the manifold system for use with compressed gas cylinders, the manifold system may employ only a single solenoid valve to switch between two different input supplies of compressed gases. In this described embodiment, the primary regulators for each input supply line may be set to produce different intermediate pressures which are fed through check valves to a common location. The single solenoid may be positioned upstream of a first check valve connected to a first primary regulator which is set to the relatively higher pressure point. When the solenoid valve is open, the relatively higher intermediate pressure of the gases output from the first primary regulator are operative to keep a second check valve associated with the second primary regulator closed. Thus, only the compressed gases from the first primary regulator are operative to flow through the system. When the solenoid valve is closed, the absence of the relatively higher intermediate pressure of gases from the first primary regulator enables the second check valve to open. Thus, the supply of compressed gases from the second primary regulator are operative to flow through the system.

BEST MODES FOR CARRYING OUT INVENTION

Figure 1:
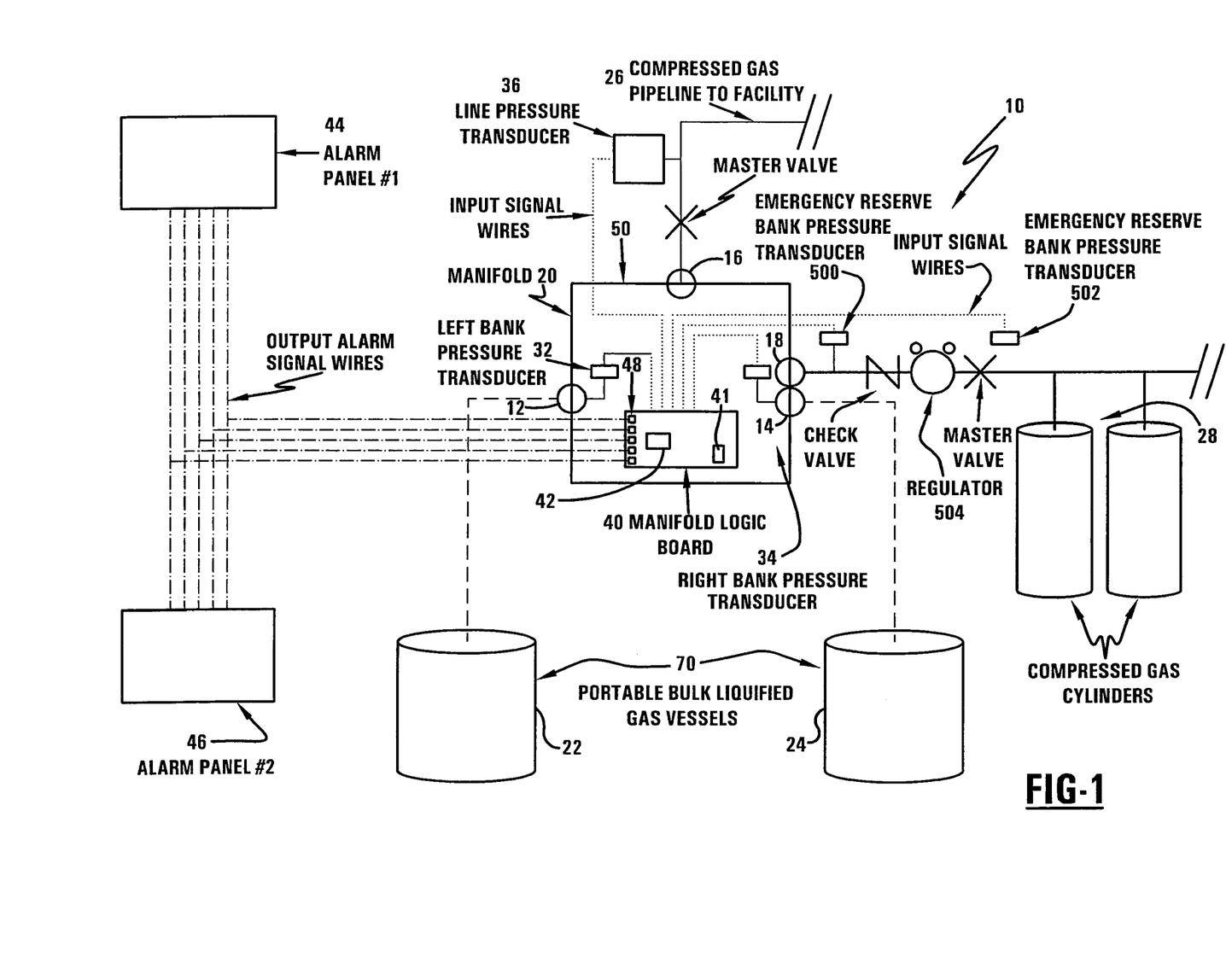
FIG. 1 is a schematic view of an exemplary embodiment of a manifold system for compressed gases for use with portable bulk liquefied gas vessels.
Figure 2:
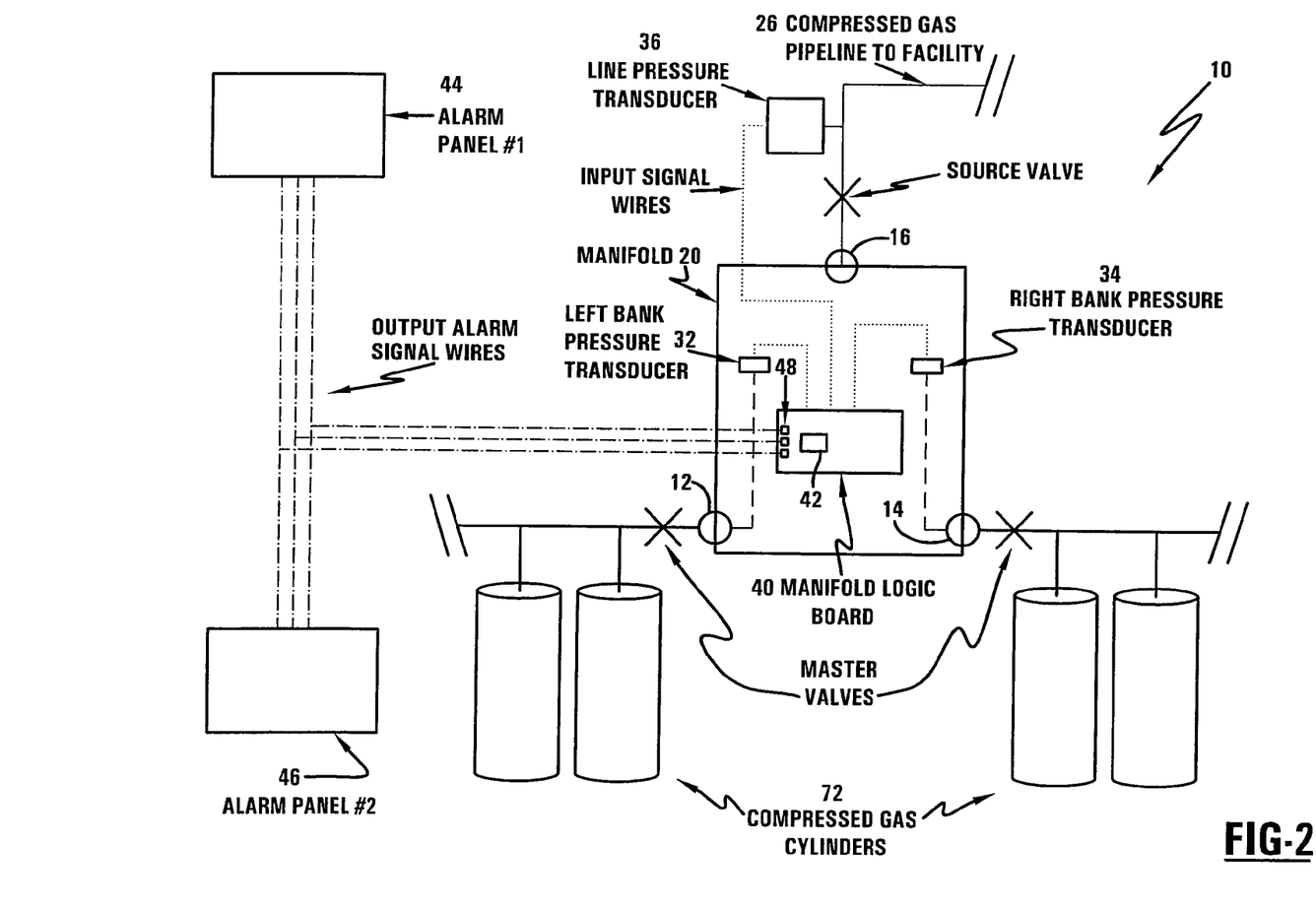
FIG. 2 is a schematic view of a further exemplary embodiment of a manifold system for compressed gases for use with compressed gas cylinders.

Referring now to the drawings and particularly to FIGS. 1 and 2 there is shown therein an exemplary embodiment of a gas supply system 10. The system 10 includes a manifold 20 with at least two gas input supply lines 12, 14 and at least one gas output supply line 16. The input supply lines 12, 14 may be adapted to releasably connect to gas supply sources 22, 24. As shown in FIG. 1 examples of gas supply sources 22, 24 may include portable bulk liquefied gas vessels 70 which include stored therein liquefied gases such as Carbon Dioxide, Helium, Hyperbaric Oxygen, Nitrogen, Nitrous Oxide, and Oxygen and other liquefied gases. As shown in FIG. 2 examples of gas supply sources 22, 24 may also include banks of compressed gas cylinders 72 which include stored therein compressed gases such as air, medical air, Carbon Dioxide, Helium, Hyperbaric Oxygen, Nitrogen, Nitrous Oxide, Oxygen, and Tri-Gas, and other compressed gases. The output supply line 16 may be adapted to releasably connect with a pipeline 26 that supplies compressed gases from the manifold to a hospital or other facility.

The exemplary embodiment of the manifold 20 is operative to selectively direct compressed gases from either the first or second input supply lines 12, 14 to the output supply line 16. The first or second input supply line which is currently activated to supply gas to the output line 16 is associated with an "In-Use" supply status. The other of the first or second input supply lines which is not associated with the In-Use supply status may be associated with a "Reserve" supply status. The exemplary embodiment of the manifold 20 is operative to detect when the gas pressure for the In-Use supply line falls below a threshold value. When this is detected, to prevent any interruption of the supply of gas to the output line 16, the manifold is operative to automatically configure the input supply lines 12 and 14 such that the input supply line corresponding to the Reserve supply begins to supply compressed gas to the output supply line 16 while the original In-Use input supply line is prevented from further supply of compressed gases to the output supply line 16.

When the switch between the input supply lines occurs, the status of the original Reserve input supply line changes to In-Use. The previous In-Use supply may then be associated with "Empty" supply status. In addition, the exemplary embodiment of the manifold may further detect when the pressure of the Empty supply has returned to a level above the threshold value. When this is detected the manifold is further operative to automatically change the status input line associated with the Empty supply status to the Reserve supply status.

Figure 3:
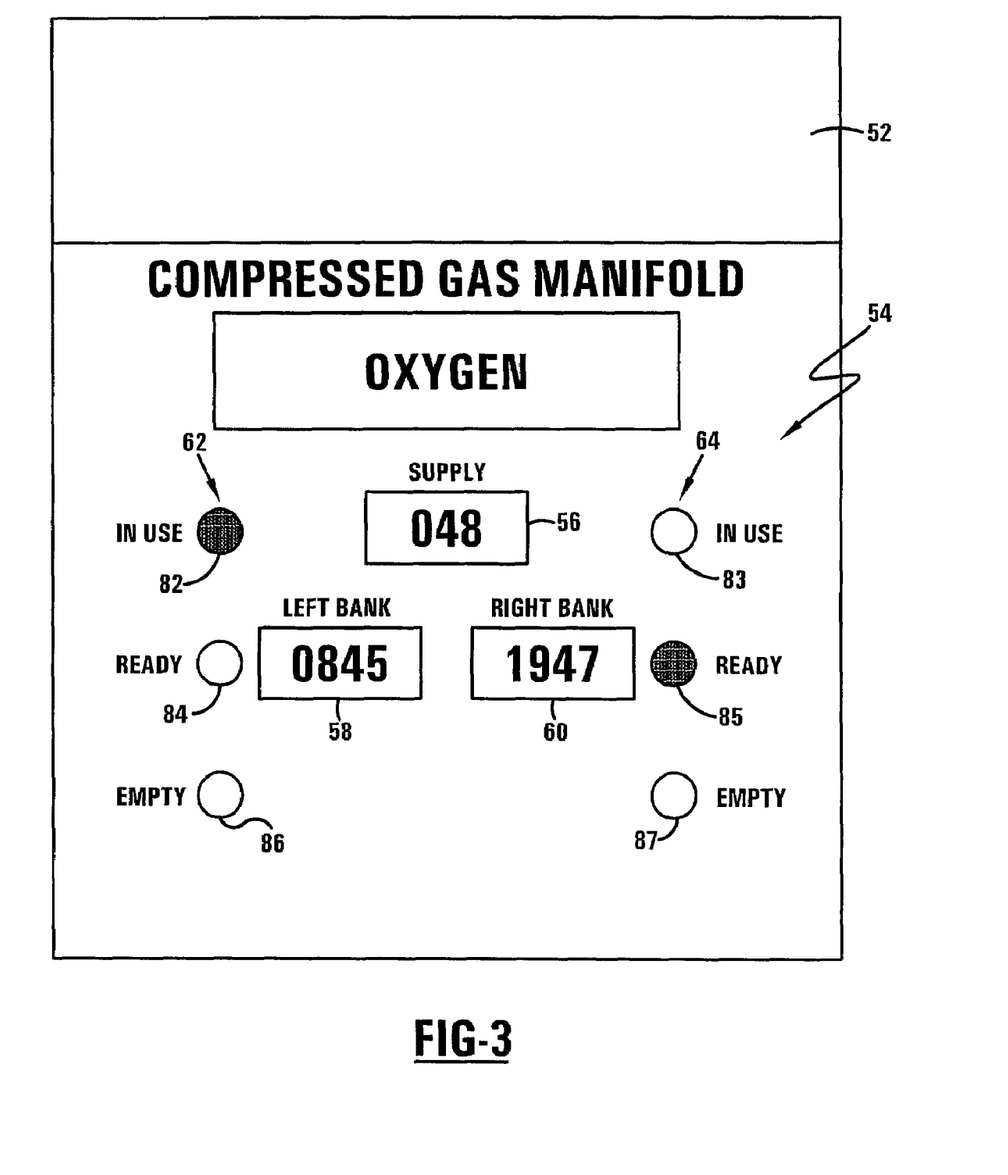
FIG. 3 is a schematic view of an exemplary embodiment of a display panel for a manifold system for compressed gases.

The exemplary embodiment of the manifold may be mounted in an enclosure 50. Such an enclosure may include an externally viewable display panel. As shown in FIG. 3, the display panel 54 may be mounted to a door or cover 52 of the enclosure and may include one or more display devices. Such display devices may output indicia representative of the pressure levels of the various input and output supply lines of the system. For example the display devices may include an output supply display device 56 which is operative to output a current pressure level for the output supply line 16. The display devices may also include a first input supply display device 58 which is operative to output a current pressure level for the first input supply line. The display devices may also include a second input supply display device 60 which is operative to output a current pressure level for the second input supply line.

In addition to indicating pressure levels, the display panel 54 may further include display devices which output the statuses associated with each of the input supply lines. For example, in an exemplary embodiment, the display panel may include a first set 62 of three LEDs associated with the first input supply line; and a second set 64 of three LEDs associated with the second input supply line. In this described exemplary embodiment, the top LEDs 82, 83 for each set of three LED's may indicate which of the input supply lines is associated with the In-Use status. In the example of the display panel 54 shown in FIG. 3 the first top LED 82 is lit (shown as black in the drawings) while the second top LED 83 is off (shown as white in the drawings). This indicates that the first supply line associated with the first top LED 82 has an In-Use status and is currently supplying compressed gases to the output supply line 16.

Also, in this described exemplary embodiment, the middle LEDs 84, 85 for each set of three LEDs indicate which of the input supply lines is associated with the Reserve status. In the example of the display panel 54 shown in FIG. 3 the second middle LED 85 is lit while the first middle LED 84 is off. This indicates that the second supply line associated with the second middle LED 85 has a Reserve status and is available to be used for supplying compressed gases to the output supply line 16 when required. The bottom LEDs 86, 87 for each set of three LED's indicate whether either of the input supply lines have a sufficiently low pressure to be associated with an "Empty" status. In the example of the display panel 54 shown in FIG. 3 neither of the first and second bottom LEDs 86, 87 are lit. This indicates that neither the first nor second supply lines associated with the first and second bottom LEDs 86, 87 have a sufficiently low pressure to be associated with the Empty status.

As shown in FIG. 1, in addition to the first and second gas supply input lines 12, 14, the manifold 20 may further include an emergency reserve input line 18. The emergency reserve input line 18 may be adapted to be releasably connect with one or more compressed gas cylinders 28 for example which may be used to supply gases to the system in instances involving an emergency, a need for maintenance, a requirement of inspection, certification testing or service of the first and second input supply lines 12, 14 and/or gas supplies 22, 24.

Figure 4:
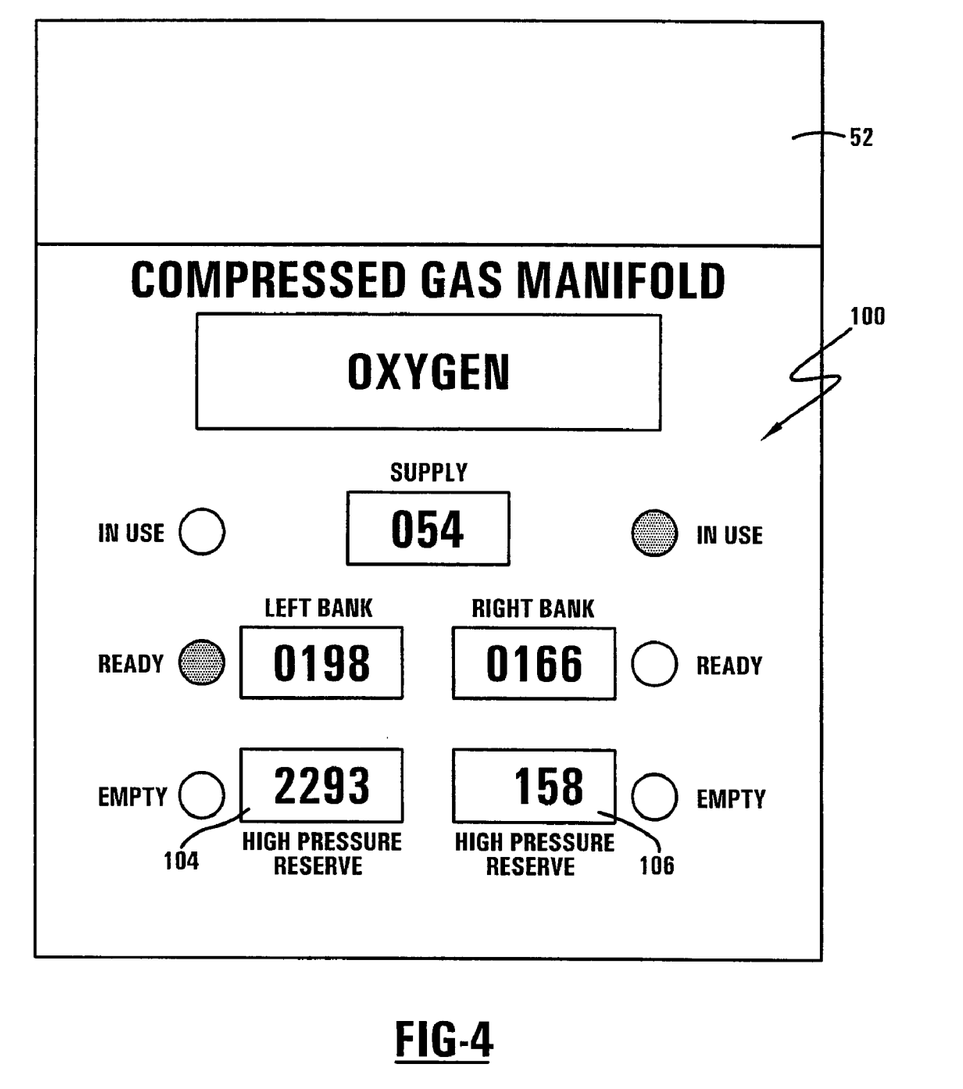
FIG. 4 is a schematic view of a further exemplary embodiment of a display panel for a manifold system for compressed gases.

FIG. 4 shows an alternative exemplary embodiment of display panel 100 for a manifold which includes an emergency reserve input line 18. Here the display panel 100 includes additional display devices 104, 106. The additional display devices may output indicia representative of the pressure levels associated with the emergency reserve. For example, the first additional display device 104 may output the high pressure level associated with the source of the emergency reserve supply 28 shown in FIG. 1. The exemplary embodiment of the system may include a pressure regulator 504 between the emergency reserve supply source 28 and the emergency reserve input supply line 18 which is operative to lower the pressure of the compressed gas at the input supply line 18 relative the initial pressure of the gas supply source 28. Referring back to FIG. 4, the second additional display device 106 may output the intermediate pressure level associated with the gas pressure at the emergency reserve supply input line 18.

Figure 5:
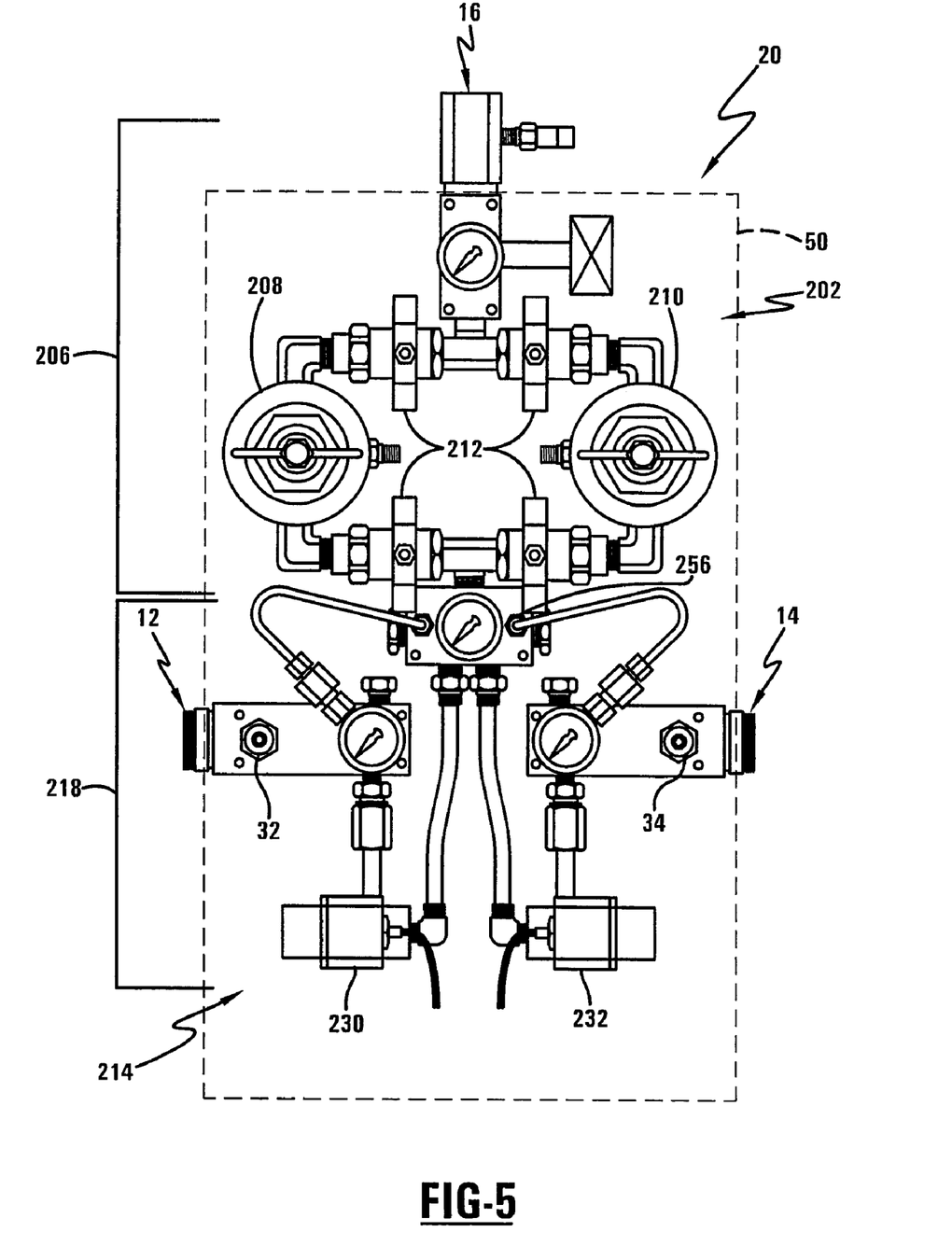
FIG. 5 is a schematic view of an exemplary embodiment of a manifold system for compressed gases in a first configuration.
Figure 6:
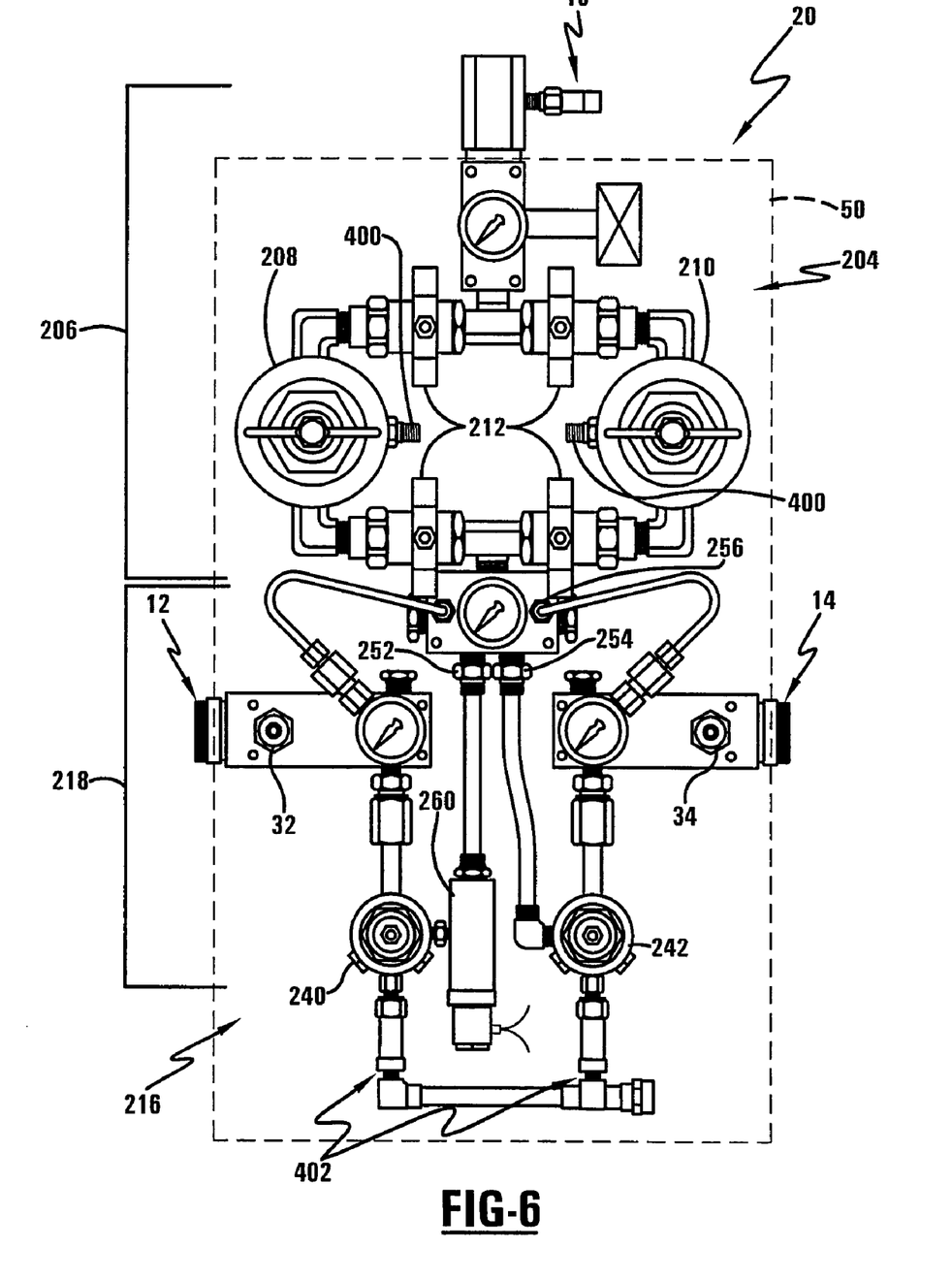
FIG. 6 is a schematic view of an exemplary embodiment of a manifold system for compressed gases in a second configuration.

FIGS. 5 and 6 show two configurations 200, 202 in which an exemplary embodiment of the manifold 20 may be configured. The manifold configuration 202 shown in FIG. 5 is operative for use with portable bulk liquefied gas supply sources. The manifold configuration 204 shown in FIG. 6 is operative for use with relatively higher pressure compressed gas cylinder supply sources. Each of these configurations may be used in the enclosure 50 of the manifold without modifying the locations of the output supply line 16, and the input supply lines 12, 14 with respect to the enclosure 50. Also in this exemplary embodiment, both configurations 202, 204 may share a common upper portion 206 which may remain unchanged for each of the configurations 202, 204. The upper portion 206 of the manifold for each configuration 200, 202 includes at least two parallel sets of line pressure regulators 208, 210 and ball valves 212. The ball valves 212 may be selectively opened and closed to direct gases through either of the pressure regulators 208, 210 to the output supply line 16. The parallel configuration of the line pressure regulators provides a redundant or backup path for the supply of gases through the upper portion 206 of the manifold for each of the configurations 200, 202.

In this described exemplary embodiment, the manifold 20 may include a lower portion 218 which is changeable between different configurations 214, 216 for each of the configurations 200, 220 of the manifold. Which configuration that is used for the manifold is based on the type and pressure of gas supply sources being connected to the input supply lines 12, 14. In the exemplary embodiment the elements that comprise the different configurations 214, 216 of the lower portion 218 may be changed out at a facility while the common elements of the manifold 20 such as the output supply line 16, the input supply lines 12, 14, and the upper portion 206, remain unchanged. Also, in an exemplary embodiment, the elements that comprise the different configurations 214, 216 of the lower portion 218 may be in releasable connection with each other. Thus a technician may perform the re-configuration of the lower portion 218 with conventional tools such as wrenches in a relatively expedient manner while the manifold remains mounted in place at a facility. Also, in an exemplary embodiment the line regulators 208,210 may be exchanged for different line regulators which provide a higher flow and/or are cryogenic in design.

For example, if the manifold 20 is initially installed at a facility for use with a relatively high pressure compressed gas cylinder supply source, the manifold configuration 204 shown in FIG. 6 may be used. If the facility chooses to install a new relatively lower pressure portable bulk liquefied gas supply vessel source, rather than replacing the original manifold 20, with a new manifold, the original manifold may remain in place and the lower portion 216 of the manifold may be re-configured to correspond to the lower portion 214 shown in FIG. 5.

In the exemplary embodiment, the configuration 214 of the lower portion 218 shown in FIG. 5 includes a pair of solenoid valves 230, 232 in operative connection with each of the input supply lines 12, 14. The solenoid valves are operative to open and close responsive to an electromagnetic signal. As will be explained in more detail below, a processor 42 of the manifold is operative to synchronize the operation of the solenoid valves to selectively control which of the input supply lines 12, 14 is enabled to supply gases to the upper portion of the 206 of the manifold. For example, when the processor detects that the pressure in the In-Use input supply line has fallen below a set threshold, the processor is operative to cause the solenoid valve associated with the current In-Use input supply line to close and is operative to cause the solenoid valve associated with the Reserve input supply line to open so as to maintain a continuous flow of gases to the output supply line 16.

The configuration 216 of the lower portion 218 shown in FIG. 6 is operative for use with relatively higher pressure compressed gas cylinders supply source. For each of the input supply lines 12, 14, this described exemplary configuration 216 includes primary regulators 240, 242. The primary regulators are operative to reduce the pressure originating from the input supply lines 12, 14 to an intermediate level which is within the pressure ranges for the elements of the manifold down stream of the primary regulators. The intermediate pressure gases exiting the pressure regulators 240, 242 are respectively directed to the upper portion 206 of the manifold. In the exemplary embodiment, the system includes two check valves 253, 254 which operate mechanically and automatically to stop a reverse flow of gas. A first one of the check valves 252 is positioned downstream of the first primary regulator 240. The second one of the check valves 254 is positioned downstream of the second primary regulator 242. In the exemplary embodiments the outputs of the check valves direct gases to a common location in the upper portion 206 of the manifold 20. In this described exemplary embodiment the common location is an intermediate pressure gauge 256. Also, in this described exemplary embodiment, the configuration 216 of the lower portion 218 of the manifold 20 includes a single solenoid valve 260 between the first pressure regulator 240 and the first check valve 252 but does not include a solenoid valve between the second pressure regulator 242 and the second check valve 254.

To enable the system to selectively control which input supply line 12, 14 is In-Use and which input supply line is in Reserve with a single solenoid valve, the exemplary embodiment is configured such that the first pressure regulator 240 is set to reduce the pressure of the gases from the first input supply line 12 to a first intermediate pressure level which is relatively higher than a second intermediate pressure level produced by the second primary regulator 242 connected to the second input supply line 14. Thus, when the solenoid valve 260 is opened responsive to the operation of the processor of the manifold, the first input supply line is associated with the In-Use status and is operative to supply compressed gas through the manifold to the output supply line. However, because the first intermediate gas pressure produced by the first pressure regulator 240 is relatively higher than the second intermediate gas pressure produced by the second pressure regulator 242, the second check valve 254 remains closed, preventing the gases from flowing into the upper portion 206 from the second input supply line 14. The second input supply line 14 thus remains unused with the Reserve status.

When the solenoid valve 260 is closed, thereby shutting off the supply of gases from the first input supply line 12, the relatively higher intermediate gas pressure from the first primary regulator 240 is no longer present to close the check valve 254, and the supply of gases into the upper portion 206 of the manifold 20 begins to be supplied from the second input supply line 14. As a result the second input supply line becomes associated with the In-Use status, and the first input supply line may become associated with the Empty status.

In an example use of the exemplary embodiment of the manifold system in which the delivery pressure of gases at the output supply line 16 is about 50 PSI, the first primary regulator 240 may be set to produce an output gas pressure of about 180 PSI while the second primary regulator 242 is set to output a gas pressure of about 120 PSI. However, it is to be understood that different configurations of the exemplary embodiment may include other differential pressures between the first and second primary regulators 240, 242 depending on the desired pressure of the output supply line 16.

As shown in FIG. 2, a compressed gas cylinders source 72 can produce relatively high pressures at the input supply lines 12, 14 in the range of 2,500 PSI for example. As shown in FIG. 6, the primary regulators 240, 242 may be operative to reduce such high inlet pressures of the gases to intermediate pressure ranges of less than 200 PSI for example. Pressure reductions of this magnitude caused by the primary regulators 240, 242 may significantly lower the temperature of the primary regulators 240, 242. To prevent the valve seats of the primary regulators from freezing up, an exemplary embodiment of the system may further include a heater device adapted to mount directly to the back portions of the primary regulators 240, 242.

Figure 7:
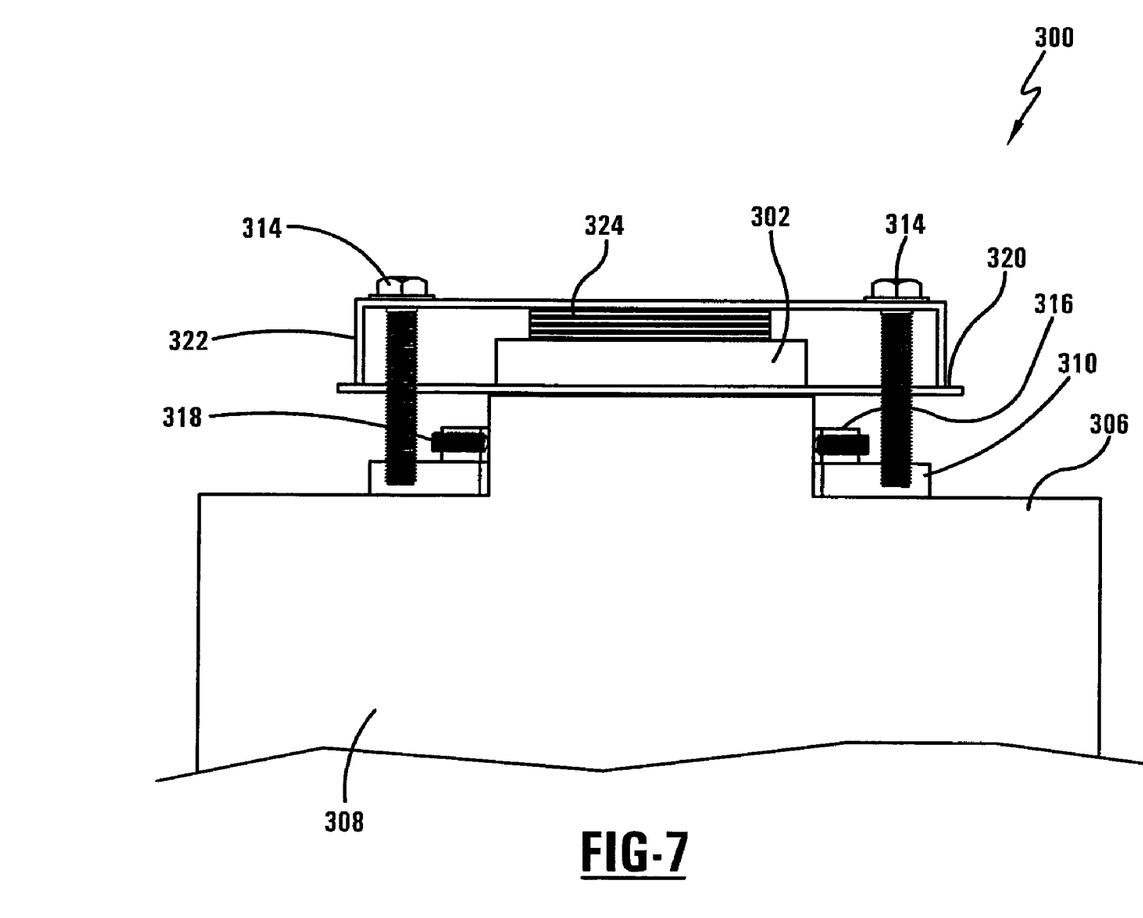
FIG. 7 is a cross sectional view of an exemplary embodiment of a heating device for a manifold system for compressed gases.
Figure 8:
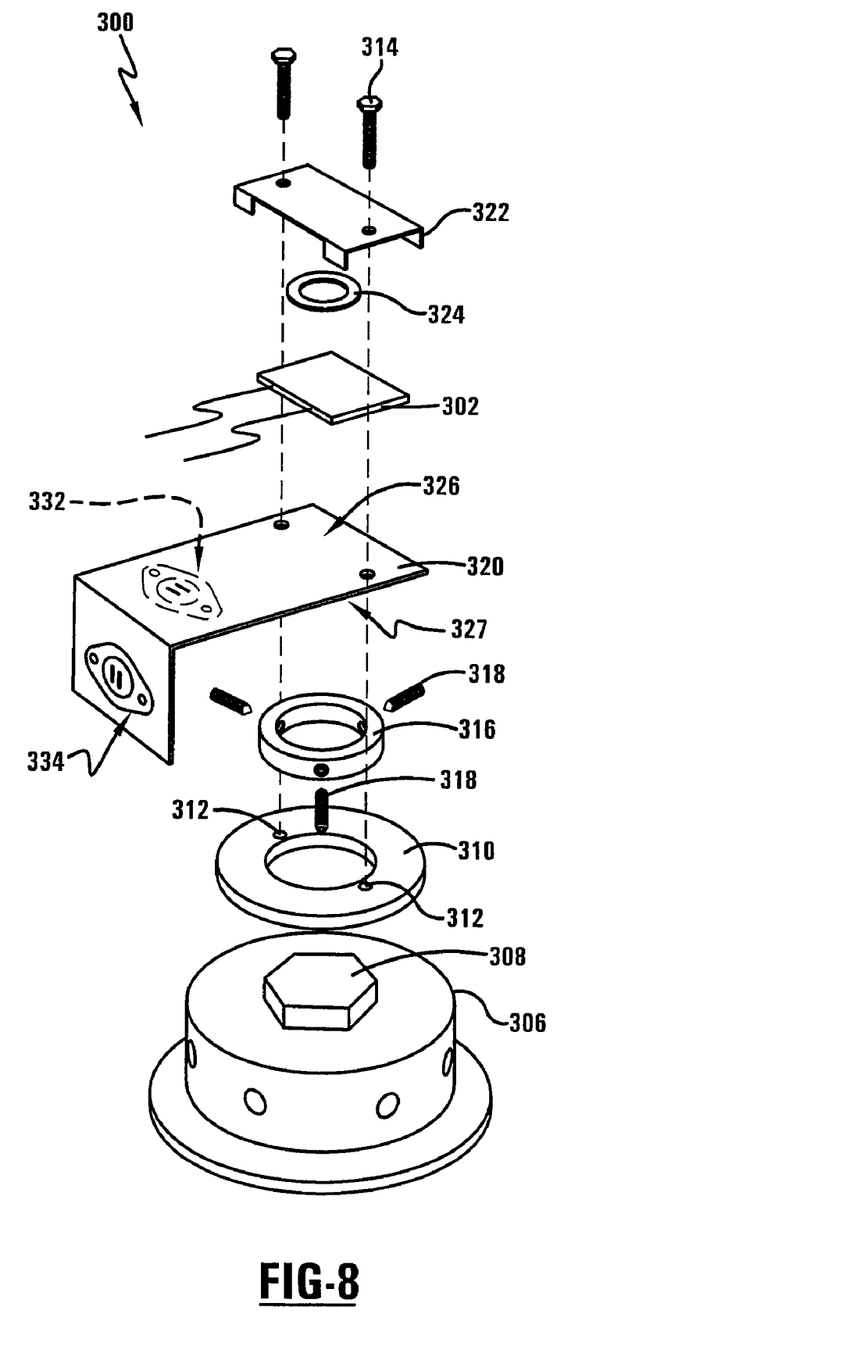
FIG. 8 is a schematic view of the assembly for the heating device.

An exemplary embodiment of such a heating device 300 mounted to a primary regulator 306 is shown in FIG. 7. A schematic assembly of the heating device 300 is shown in FIG. 8. In this described exemplary embodiment the heating device 300 includes a heating element 302 such as a ceramic heater or other electrically controlled heating element. The heating device is operative to mount the heating element adjacent the back of a primary regulator 306. As shown in FIG. 8 the heating device 300 is operative to releasably mount to the hexagonal portion 308 located on the back of the regulator 306. The hexagonal portion may house or be adjacent to the valve seat of the pressure regulator.

For this purpose the exemplary embodiment of the heating device may include a joining plate 310 with at least two threaded holes 312 which are operative to cooperatively receive joining screws 314. The heating device may further include a lock ring 316 with a plurality of locking set screws 318. When both the joining plate and the lock ring are positioned around the hexagonal portion 308, the locking set screws 318 may be screwed inwardly to mechanically lock the lock ring and joining plate to hexagonal portion 308.

In the exemplary embodiment the ceramic heater 302 is sandwiched between a thermostat bracket 320 and a clamp bracket 322. A wave spring 324 may further be included to maintain the ceramic heater 302 in engagement with the upper surface 326 of the thermostat bracket. In the exemplary embodiment the joining screws 314 pass through apertures in the clamp bracket and the thermostat bracket and are threaded into the holes 312 of the joining plate to lock the heating device together on the primary regulator 306. In this configuration the opposed face 327 of the thermostat bracket 320 is in physical contact with the top surface of the hexagonal portion 308. As a result the ceramic heater 302 and the described bracketry 330 are in direct physical contact with the back of the primary regulator 306 and is operative to transfer heat energy directly to the primary regulator 306. The described heating device 300 may operate at about 100 watts to prevent the valve seat of a primary regulator from freezing up.

Referring back to FIG. 1, the exemplary embodiment of the manifold 20 may include a first input supply transducer 32 in operative connection with the first input supply line 12. The manifold 20 may also include a second input supply transducer 34 in operative connection with the second input supply line 14. The manifold 20 may also include a third output supply transducer 36 in operative connection with the output supply line 16 of the manifold or the pipeline 26 to the facility.

The first, second and third transducers 32, 34, 36 are operative to provide electrical signals representative of the gas pressures within the respective first and second gas supply input lines 12, 14 and output supply line 16. The exemplary embodiment of the manifold 20 may further includes a logic board 40. The logic board 40 may include the processor 42 in operative connection with the first, second and third transducers 32, 34, 36.

In the described exemplary embodiment, the processor 42 is operative responsive to the electrical signals from the transducers 32, 34, 36 to output corresponding pressure levels through the previously described display devices 58, 60, 56 of the display panel 54. In the exemplary embodiment the logic board may include a jumper pin block, dip switch or other selection device which enables an operator to select the desired pressure units of measurement for the display devices 58, 60, 56. For example, in the described exemplary embodiment, the processor may be responsive to the selection device on the logic board to calculate and output pressure units of measurement corresponding to PSIG, kPa, or BAR.

In addition, in the described exemplary embodiment, the processor 42 is responsive to the transducers 32 and 36 to control the operation of the two solenoid valves 230, 232 of the manifold configuration 202 shown in FIG. 5 or the single solenoid valve 260 of the manifold configuration 204 shown in FIG. 6. The processor is operative to set the previously described statuses of "In-Use," "Reserve," and "Empty" for the first and second input supply lines 12, 14 responsive to the pressure signals produces by the transducers 32, 36 and responsive to the open and closed condition of the one or more previously described solenoid valves. The processor is further operative to cause the previously described sets of "In-Use," "Reserve," and "Empty" LEDs 62, 64 shown in FIG. 3 to turn on and off responsive to the determined statuses associated with the first and second input supply lines. In addition, the processor is further operative to control the open or closed position of the solenoid valve or valves to selectively switch the supply of compressed gassed from the In-Use input supply line to the Reserve input supply line responsive to transducer associated with the In-Use input supply line indicating a pressure drop below a minimum threshold value.

As shown in FIG. 1, for systems that include an Emergency Reserve, the system may also include a first transducer 500 in operative connection with the Emergency Reserve input line 18. The first transducer 500 is operative to measure the gas pressure corresponding to the in use pressure for the emergency reserve down stream of the emergency Reserve regulator 504. In addition the system may also include a second transducer 502 in operative connection with compressed gas cylinders of the emergency reserve supply source 28. The second transducer 502 is operative to measure the gas pressure corresponding to the pressure for the emergency reserve gas supply upstream of the emergency Reserve regulator 504. The outputs of the first transducer 500 and second transducer 502, may be monitored by the processor for use with displaying corresponding pressure values through the intermediate pressure reserve display device 106 and the high pressure reserve display device 104 respectively as shown in FIG. 4.

In the exemplary embodiment the logic board 40 may further include a plurality of relays 48. The relays may be placed in operative connection with the alarm devices of one or more alarm panels 44, 46. The alarm panels 44, 46 may include audible and/or visual alarm devices which are selectively controlled by the processor through the triggering of the relays on the logic board. In one exemplary embodiment, the processor 42 is operative responsive to the electrical signals of the transducers to trigger the relays 48 between open and closed positions so as to activate the alarm devices of the alarm panels 44, 46. For example, in an exemplary embodiment, the processor may be operative to compare the pressure signals from the transducers to low and high threshold values and trigger corresponding alarms when the threshold values are breached. For example, when the gas pressure measured by the line pressure transducer 36 drops sufficiently to send the electrical signals from the one transducer to a level indicative of the pressure being below the associated low threshold value, the exemplary embodiment of the processor 42 is operative to trigger one or more relays 48 which causes an alarm device to provide an alarm signal indicative of the pressure for the line pressure to the facility having fallen below an acceptable value. Likewise, when the gas pressure measured by the transducer 36 increases sufficiently to send the electrical signals from the one transducer to a level indicative of the pressure being above the associated high threshold value, the exemplary embodiment of the processor 42 is operative to trigger one or more relays 48 which cause an alarm device to provide an alarm signal indicative of the pressure for the line pressure to the facility having risen above an acceptable value. In the exemplary embodiment, the logic board relays may correspond to the following alarm signal outputs which are individually activated by the processor responsive to the transducers and the states of the one or more solenoids: Low Line Pressure; High Line Pressure; Secondary In Use; Emergency Reserve In Use, Emergency Reserve Low.

In the exemplary embodiment the processor may be programmed with or may be operative to access from a memory, a plurality of sets of high and low pressure threshold values. Each set may correspond to a different type of manifold use and/or different type of compressed gas. In the exemplary embodiment, the logic board may include a selection device 41 which enables a user to select which set of threshold values should be used by the processor when determining when to activate the alarm relays. Examples of selection devices may include DIP switches, jumpers, dials, or any other type of input device which can be manipulated by a user.

In the exemplary embodiment the heating device may further include a fixed thermostat 332 and a resettable thermostat 334 in operative connection with the thermostat bracket 320. The repeatable thermostat may act as a redundant thermostat in the event the fixed thermostat fails. These thermostats may be operatively configured in a circuit which is operative to control the output of heat by the heating device. The circuit may be operative to prevent the heating device from overheating the regulator, when a temperature measured by at least one of the thermostats reaches or exceeds a predetermined level. In the exemplary embodiment, when the resettable thermostat pops off (i.e. disengages the heater), it must be manually reset to enable the heater to turn on.

In the exemplary embodiment the line pressure regulators 208, 210 shown in FIG. 6 for example may include DISS demand valves 400. The DISS demand valves may be used to bleed line pressure during service and as emergency feed ports for the system. An example of a system and method of using DISS demand valves 400 in this manner is shown in U.S. Pat. No. 6,305,400 B1 of Oct. 23, 2001 which is incorporated by reference herein in its entirety.

In the exemplary embodiment of the manifold configuration 204 shown in FIG. 6, the lower portion of the manifold 218 may further include intermediate pressure relief valves 402 in operative connection with the primary regulators 240, 242. Also, in the exemplary embodiment of the manifold configuration 202 shown in FIG. 5, the lower portion 218 of the manifold system may include economizer circuits between the input supply lines 12, 14 and the intermediate pressure gauge 256. The economizer circuits include mechanical piping circuits which allow built up reserve gas to be used in low volume rather than allowing the gas to vent to atmosphere.

Thus the new manifold system and method for compressed gases achieves one or more of the above stated objectives, eliminates difficulties encountered in the use of prior devices and systems, solves problems and attains the desirable results described herein.

In the foregoing description certain terms have been used for brevity, clarity and understanding, however no unnecessary limitations are to be implied therefrom because such terms are used for descriptive purposes and are intended to be broadly construed. Moreover, the descriptions and illustrations herein are by way of examples and the invention is not limited to the exact details shown and described.

In the following claims any feature described as a means for performing a function shall be construed as encompassing any means known to those skilled in the art to be capable of performing the recited function, and shall not be limited to the features and structures shown herein or mere equivalents thereof. The description of the exemplary embodiment included in the Abstract included herewith shall not be deemed to limit the invention to features described therein.

Having described the features, discoveries and principles of the invention, the manner in which it is constructed and operated, and the advantages and useful results attained; the new and useful structures, devices, elements, arrangements, parts, combinations, systems, equipment, operations, methods and relationships are set forth in the appended claims.

We claim:

1. A manifold system for compressed medical gases comprising:
   at least one input supply line adapted to receive a supply of medical gas therein from at least one compressed gas cylinder;
   at least one output supply line coupled to receive medical gas from the at least one first input supply line;
   at least one pressure regulator between the output supply line and the at least one input supply line, wherein the pressure regulator includes a housing and a valve seat within the housing, wherein the housing includes a hexagonal portion, wherein the hexagon portion houses the valve seat;
   a heating device releasably mounted to the hexagonal portion, wherein the heating device includes a lock ring, wherein the lock ring is mounted around the hexagonal portion.

2. The system according to claim 1, wherein the lock ring includes a plurality of set screws in threaded connection with the lock ring, wherein the set screws are operative to move inwardly within an aperture of the lock ring into engagement with the hexagonal portion.

3. The system according to claim 1, wherein the heating device includes a heating element, wherein the heating device is operative to bias the heating element to move toward a top face of the hexagonal portion.

4. The system according to claim 3, wherein the heating device includes a thermostat bracket between the heating element and the top face of the hexagonal portion, wherein the thermostat bracket includes at least one thermostat that is operative to control an output of heat by the heating element.

5. The system according to claim 4, wherein the thermostat bracket includes at least two thermostats operative to control the output of heat by the heating element.

6. The system according to claim 5, wherein at least one of the thermostats is a re-settable thermostat that is operative to cause the heating device to be turned off when the re-settable thermostat detects a predetermined temperature level, wherein the re-settable thermostat must be manually reset to enable the heating device to turn on.

7. The system according to claim 4, wherein the heating device further comprises:
   a clamp bracket mounted adjacent the heating element; and
   a spring positioned between the clamp bracket and the heating element, wherein the spring is operative to bias the heating element against the thermostat bracket.

8. The system according to claim 7, wherein the heating device further includes a joining plate adapted to mount around the hexagonal portion, wherein the joining plate is positioned between the pressure regulator and the lock ring, wherein further comprising at least two joining screws adapted to secure the clamp bracket to the joining plate.

9. The system according to claim 1, wherein the supply of compressed medical gas corresponds to at least one of medical air, Carbon Dioxide, Helium, Hyperbaric Oxygen, Nitrogen, Nitrous Oxide, and Oxygen.

10. A manifold system for compressed medical gases comprising:
    at least one input supply line adapted to receive a supply of medical gas therein from at least one compressed gas cylinder;
    at least one output supply line coupled to receive medical gas from the at least one first input supply line;
    at least one pressure regulator, wherein the at least one pressure regulator is mounted between the at least one input supply line and the at least one output supply line, wherein the pressure regulator includes a hexagonal portion;
    at least one heating device clamped to the hexagonal portion, wherein the heating device includes a heating element and a spring, wherein the spring is operative to urge the heating element toward the hexagonal portion; and
    at least one thermostat in operative connection with the heating device, wherein the thermostat is operative to control the output of heat by the heating device in response to a temperature level measured by the thermostat.

11. The system according to claim 10, further comprising a thermostat bracket between the heating element and a top face of the hexagonal portion, wherein the at least one thermostat is in operative connection with the thermostat bracket.

12. The system according to claim 11, wherein the hexagonal portion houses a valve seat of the pressure regulator.

13. The system according to claim 12, wherein the heating device includes a lock ring, wherein the lock ring is adapted to mount around the hexagonal portion in releasable engagement with the hexagonal portion.

14. The system according to claim 13, wherein the supply of compressed medical gas corresponds to at least one of medical air, Carbon Dioxide, Helium, Hyperbaric Oxygen, Nitrogen, Nitrous Oxide, and Oxygen.

* * * * *